(12) United States Patent
Saddow et al.

(10) Patent No.: US 12,376,776 B1
(45) Date of Patent: Aug. 5, 2025

(54) FLEXIBLE MONOLITHIC ALL POLYCRYSTALLINE SILICON CARBIDE NEURAL INTERFACE DEVICE AND METHOD OF MANUFACTURE

(71) Applicant: University of South Florida, Tampa, FL (US)

(72) Inventors: Stephen Edward Saddow, Land O Lakes, FL (US); Francesco La Via, Catania (IT); Christopher Leroy Frewin, Ann Arbor, MI (US)

(73) Assignees: University of South Florida, Tampa, FL (US); CNR Institute for Microelectronics and Microsystems, Catania (IT); NeuroNexus, Ann Arbor, MI (US)

( * ) Notice: Subject to any disclaimer, the term of this patent is extended or adjusted under 35 U.S.C. 154(b) by 859 days.

(21) Appl. No.: 17/471,386

(22) Filed: Sep. 10, 2021

Related U.S. Application Data

(60) Provisional application No. 63/076,431, filed on Sep. 10, 2020.

(51) Int. Cl.
*A61B 5/00* (2006.01)
*A61B 5/263* (2021.01)
(Continued)

(52) U.S. Cl.
CPC .............. *A61B 5/293* (2021.01); *A61B 5/263* (2021.01); *A61B 5/6868* (2013.01);
(Continued)

(58) Field of Classification Search
CPC .......... A61B 5/291–293; A61B 5/6868; A61B 5/263–268; A61N 1/0529; A61N 1/0531
See application file for complete search history.

(56) References Cited

U.S. PATENT DOCUMENTS

| | | | |
|---|---|---|---|
| 9,211,401 B2 | 12/2015 | Frewin et al. | |
| 10,136,825 B2 | 11/2018 | Frewin et al. | |
| 2012/0232631 A1* | 9/2012 | Frewin ..................... | A61B 5/24 607/116 |

OTHER PUBLICATIONS

Bernardin, Evans K., "Demonstration of Monolithic-Silicon Carbide (SiC) Neural Devices" (Nov. 2018). USF Tampa Graduate Theses and Dissertations. (Year: 2018).*

(Continued)

*Primary Examiner* — Linda C Dvorak
*Assistant Examiner* — Davina E. Lee
(74) *Attorney, Agent, or Firm* — Molly L. Sauter; Smith & Hopen, P.A.

(57) ABSTRACT

An implantable, conformal, neural interface device fabricated completely from neuro-compatible SiC and method of manufacture thereof, includes at least one elongated probe to be placed in a brain of a subject of interest, the at least one elongated probe comprising a plurality of electrodes positioned on a surface of the elongated probe, each of the plurality of electrodes comprising a conductive mesa consisting of polycrystalline silicon carbide (SiC), an insulative layer consisting of amorphous SiC, the insulative layer positioned to surround the conductive mesa absent a window through the amorphous SiC exposing a surface of the conductive mesa. The elongated probe is integral with, the probe base comprising a plurality of contact pads, each of the plurality of contact pads in electrical communication with one of the plurality of electrodes.

3 Claims, 4 Drawing Sheets

(51) Int. Cl.
*A61B 5/293* (2021.01)
*H01L 21/02* (2006.01)
*H01L 21/04* (2006.01)
*H10D 62/832* (2025.01)
*G06F 3/01* (2006.01)

(52) U.S. Cl.
CPC .. *H01L 21/02167* (2013.01); *H01L 21/02381* (2013.01); *H01L 21/02488* (2013.01); *H01L 21/02529* (2013.01); *H01L 21/02576* (2013.01); *H01L 21/02675* (2013.01); *H01L 21/0455* (2013.01); *H01L 21/0475* (2013.01); *H10D 62/8325* (2025.01); *A61B 2562/0209* (2013.01); *A61B 2562/125* (2013.01); *A61B 2562/164* (2013.01); *A61B 2562/166* (2013.01); *G06F 3/015* (2013.01)

(56) References Cited

OTHER PUBLICATIONS

Diaz-Botia, C. A. et al., "A silicon carbide array for electrocorticography and peripheral nerve recording" (Aug. 2017). Journal of Neural Engineering, vol. 14. (Year: 2017).*
Bernardin, E. K., Demonstration of Monolithic-Silicon Carbide (SiC) Neural Devices (2018). Graduate Theses and Dissertations. https://scholarcommons.usf.edu/etd/7474.
Diaz-Botia, C. A. Silicon carbide technologies for interfacing with the nervous system (2017). UC Berkeley Electronic Theses and Dissertations, https://escholarship.org/uc/item/35w3d01b.
Jovanovic, P. et al., Electrochemical Dissolution of Iridium and Iridium Oxide Particles in Acidic Media: Transmission Electron Microscopy, Electrochemical Flow Cell Coupled to Inductively Coupled Plasma Mass Spectrometry and X-ray Absorption Spectroscopy Study (2017). Journal of the American Chemical Society, 139 (36), 12837-12846, DOI: 10.1021/jacs.7b08071.
Bernardin, E. K., et al., Demonstration of a Robust All-Silicon-Carbide Intracortical Neural Interface (2018). Micromachines, 9, 412; doi: 10.3390/mi9080412.
Deku, F. et al., Amorphous Silicon Carbide Platform for Next Generation Penetrating Neural Interface Designs (2018). Micromachines, 9, 480; doi: 10.3390/mi9100480.

* cited by examiner

FLEXIBLE MONOLITHIC ALL POLYCRYSTALLINE SILICON CARBIDE NEURAL INTERFACE DEVICE AND METHOD OF MANUFACTURE

CROSS-REFERENCE TO RELATED APPLICATIONS

This application is a continuation of and claims priority to U.S. Provisional Patent Application No. 63/076,431, filed Sep. 10, 2020 and entitled "A FLEXIBLE MONOLITHIC ALL-SiC NEURAL INTERFACE FOR BOTH IMPLANTABLE AND SURFACE BI-DIRECTIONAL NEURAL SIGNAL TRANSDUCTION," which is incorporated by reference in its entirety.

BACKGROUND OF THE INVENTION

Silicon is known to be used in the manufacturing of bi-polar junction transistors, junction field effect transistors and metal insulator transistor devices. Field effect devices constructed from silicon and silicon dioxide have been used to interact with neurons by receiving and sending signals. Field effect devices, unlike electrode-based devices, use a high electrical impedance to influence the electrochemical environment within the body. Unfortunately, field effect devices are ineffective for use over long periods of time for several reasons. One known disadvantage to field effective devices is that sodium ions may diffuse through the oxide and create a fixed positive charge at the interface, which is an undesirable result. More importantly, silicon and silicon oxide have been proven to be non-biocompatible for use as an implantable neural device.

The majority of semiconductors which could replace silicon are also known to be toxic. However neural devices must, by necessity, be implanted permanently so they must be very robust and, to date, a semiconductor-based neural device, such as a brain-machine interface (BMI), has failed to perform adequately for long-term chronic implantations. The field of implantable brain machine interfaces (BMIs), also known as brain computer interfaces (BCIs), is a burgeoning technology developed by engineers, neurologists, and computer scientists that has the potential to offer hope and possible cures for many problems associated with the central nervous system. BMI and BCI devices allow reception of electrical pulses generated by neurons and transfer of the electrical pulses to external devices where they may be used as control signals for the nervous system. BMI devices known in the art utilize penetrating, invasive interfaces directly accessing the signals from nearby neurons. The proximity of the BMI device to these neurons also allows the direct stimulation of these signals, known as action potentials, and can thereby create true closed loop control systems. Implantable devices, such as BMIs, inherently possess a larger content and quality of information, and therefore can easily outperform other interface techniques such as electroencephalography (EEG) and electrocorticography (ECG). Although implantable devices allow for closed loop control and sensory feedback, and the information they acquire can control complicated BMI systems, these systems still experience major difficulties which are blocking their widespread usage.

Implantable biocompatible devices utilizing crystalline silicon carbide (SiC) are known in the art. However, the known devices require high-temperature manufacturing techniques and are high-cost. The known SiC implants made from cubic SiC (known as 3C-SiC) also suffer from the low breakdown voltage of the required diode junction layers. Manufacturing of hexagonal SiC (4H- or 6H-SiC) is expensive due to the need to fabricate the device on expensive SiC substrates, while 3C-SiC can be grown on inexpensive Si substrates and using SOI (silicon-on-insulator) technology.

Accordingly, what is needed in the art is an improved implantable biocompatible neural device. Additionally, a method of manufacturing such a device at a reduced cost is also needed in the art.

SUMMARY OF INVENTION

In various embodiments, the present invention utilizes polycrystalline SiC, formed at low manufacturing temperatures and using either in-situ or laser dopant activation, to provide a thin, highly flexible, stack of SiC layers that are monolithic in nature and that can be easily formed into both surface electrodes (i.e., Electrocorticography (ECoG) interfaces) and implantable electrodes (i.e., Intracortical Neural Interfaces (INI)). This invention solves performance, flexibility and cost issues that are inherent in the known prior art solutions.

In one embodiment, an implantable neural interface device for placement to provide neural signal transduction with a brain of a subject of interest is provided. The device includes, at least one elongated probe to be placed in a brain of a subject of interest, the at least one elongated probe includes a plurality of electrodes positioned on a surface of the elongated probe. Each of the plurality of electrodes includes a conductive mesa consisting of polycrystalline silicon carbide (SiC) and an insulative layer consisting of amorphous SiC. The insulative layer is positioned to surround the conductive mesa absent a window through the amorphous SiC exposing a surface of the conductive mesa. The device further incudes, a probe base integral with the elongated probe, the probe base comprising a plurality of contact pads, each of the plurality of contact pads in electrical communication with one of the plurality of electrodes.

The device may further include one or more electrical traces connecting the plurality of electrodes to the contact pads of the probe base wherein the one or more electrical traces are composed of polycrystalline SiC. The probe base of the device may additionally include a plurality of electronic components coupled to one or more of the contact pads.

One method of manufacturing the implantable neural interface device includes, providing a silicon (Si) wafer coated with an oxide layer, depositing a first insulating a-SiC layer on a surface of the Si wafer, depositing a poly-Si layer adjacent to the a-SiC layer, forming a conductive n-type poly-SiC layer from the poly-Si layer, forming conductive mesas from the n-type poly-SiC layer, depositing a second a-SiC insulating layer to surround the conductive mesas, forming windows through the second a-SiC insulating layer to expose a portion of each of the conductive mesas, etching the first insulating a-SiC layer, the poly-Si layer, the second insulating a-SiC layer and the oxide layer to define the elongated probe and releasing the elongated probes from the Si wafer using hydrofluoric acid (HF) processing.

In one embodiment, the conductive n-type poly-SiC layer from the poly-Si layer may be grown from the poly-SiC by doping about 2 µm of the poly-Si layer with nitrogen ($N_2$) during the growing of the poly-Si layer to form the conductive n-type poly-SiC layer. Alternatively, the conductive n-type poly-SiC layer may be formed from the poly-Si layer by growing an undoped poly-SiC layer, laser doping the undoped poly-SiC layer and then annealing the undoped poly-SiC layer to form the conductive n-type poly-SiC layer.

Another method of manufacturing the implantable neural interface device includes, providing a silicon (Si) wafer coated with an oxide layer, depositing a first insulating a-SiC layer on a surface of the Si wafer, laser doping/recrystalizing about 2 μm of the first a-SiC insulating layer to form a doped poly-SiC layer on the surface of the Si wafer, forming conductive mesas from the doped poly-SiC layer, depositing a second a-SiC insulating layer to surround the conductive mesas, forming windows through the second a-SiC insulating layer to expose a portion of each of the conductive mesas, etching the first insulating a-SiC layer, the doped poly-Si layer, the second insulating a-SiC layer and the oxide layer to define the elongated probes and releasing the elongated probes from the Si wafer using hydrofluoric acid (HF) processing.

An additional method of manufacturing the implantable neural interface device includes, providing two silicon (Si) wafers coated with an oxide layer, depositing a first insulating a-SiC layer on a surface of a first one of the Si wafers, growing a poly-SiC layer on a second one of the Si wafers, bonding the a-SiC layer of the first Si wafer to the poly-SiC layer of the second Si wafer using a thermo-compression bond, removing the silicon and oxide layers of the second Si wafer using hydrofluoric acid (HF) processing, forming conductive mesas from the poly-SiC layer of the second Si wafer, depositing a second a-SiC insulating layer to surround the conductive mesas, forming windows through the second a-SiC insulating layer to expose a portion of each of the conductive mesas, etching the first insulating a-SiC layer, the doped poly-Si layer, the second insulating a-SiC layer and the oxide layer to define the elongated probes and releasing the elongated probes from the Si wafer using hydrofluoric acid (HF) processing.

Accordingly with the various embodiments, using advanced silicon carbide thin film processes, a novel, thin, fully monolithic neural implant has been devised to allow for highly flexible neural interfacing, both for implantation into (implantable), and resting on (ECoG), the brain for bi-directional neural electrical signal transduction. The invention utilizes only low-temperature, thin-film methods to fabricate a neural interface that is much lower in cost and allows for a higher flexibility device that can be both implanted into brain tissue while also resting on the surface of the brain, below the scalp.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In various embodiments, the present invention provides for the use of exclusively polycrystalline and amorphous SiC, in its crystalline form, to provide for various embodiments of a flexible implantable neural device.

Unlike silicon and diamond, silicon carbide has more than 250 different crystalline stacking formations, each with unique electrical and optical properties. These formations are referred to as polytypes and have been utilized primarily in the power electronics industry. The different properties for SiC polytypes differentiate its use from other IV-IV semiconductors by allowing additional complexity in device manufacturing. In other words, using a polytype like cubic silicon carbide will not be expected to work the same way if interchanged with hexagonal silicon carbide. The growth during the manufacturing process of the single crystalline material is different than for non-crystalline forms, requiring high temperatures which excludes the inclusion of most metallic or polymeric materials during processing.

The present invention establishes that polycrystalline and amorphous SiC can be fabricated at lower temperatures and by less expensive processes. These materials are different than the single crystalline forms in electrical properties but still retain their physical strength and chemical resilience. Amorphous SiC, a-SiC, is not a conductive material and with careful growth processing can be an excellent low-K dielectric with high blocking voltages. Polysilicon carbide can be doped to ensure high electrical conductivity, and while it may not be as electrically ideal as single crystal SiC, especially for complicated field effect transistors, it can provide a platform for both trace wiring and electrode sites.

Thus, the present invention uses two, non-single, crystalline forms of SiC to fabricate neural implants with traces and electrodes composed of polycrystalline SiC and insulation composed of amorphous SiC. While these devices are not formed from a single piece of material, the similar material interfaces are capable of adequately bonding through the actual deposition process and subsequent processing techniques, like rapid thermal annealing.

Figure 1:
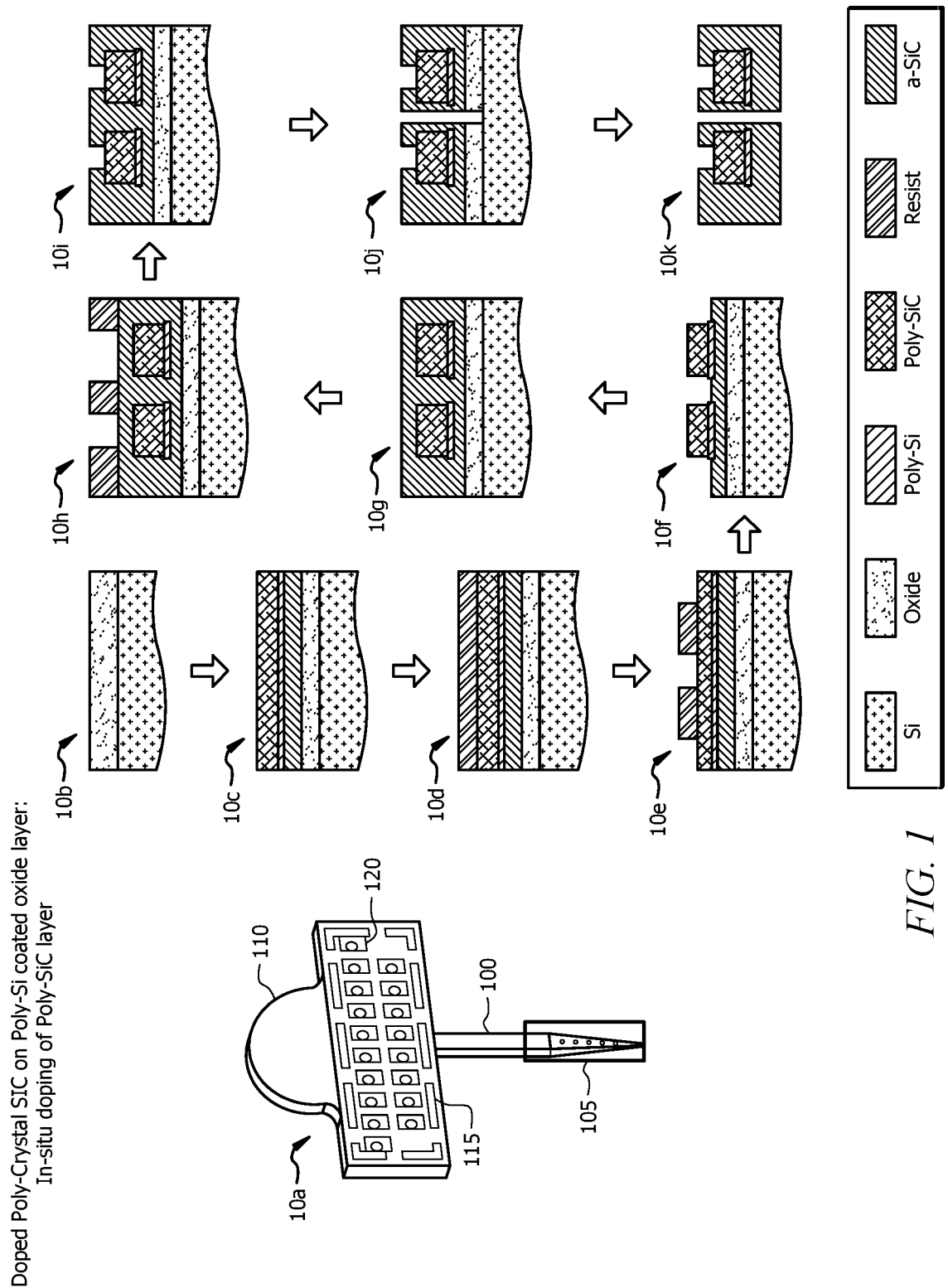
FIG. 1 illustrates an all-SiC fabrication process flow to fabricate implantable devices wherein the conductive poly-SiC layer is formed by in-situ doping during the growth of the layer, in accordance with an embodiment of the present invention.

FIG. 1 illustrates a first exemplary all-SiC fabrication process flow for the fabrication of a Michigan-style flexible monolithic all poly-SiC neural interface device 10a. The implantable neural interface device 10a provides for neural signal transduction with a brain of a subject of interest. The finished device 10a includes an elongated shaft 100 comprising a plurality of electrodes 105 formed by the illustrated process steps shown in 10b-10k and a probe base 110 integral with the elongated probe 100, the probe base 110 includes a plurality of contact pads 120, each of the plurality of contact pads 120 in electrical communication with one of the plurality of electrodes 105 via traces formed between the contact pads 120 and the electrodes 105. Various electronics for signal generation, switching control, signal filtering, digitization, wireless transmission, and power control may be coupled to the plurality of contact pads 120 of the probe base.

As illustrated in FIG. 1, the exemplary fabrication process flow begins at 10b by providing an oxide-coated Si wafer. A thick (~4 μm) a-SiC layer was then deposited via plasma-enhanced chemical vapor deposition (PECVD), followed by the deposition of ~100 nm layer of poly-Si, followed by the growth of poly-SiC (doped with $N_2$ during growth) of ~2 μm to form conductive n-type poly-SiC at 10c. At 10d, the wafer was coated with photoresist and at 10e the photoresist was patterned via photolithography. At 10f a deep reactive-ion etching (DRIE) process was used to form the conductive mesas of poly-SiC followed by a thermal/laser anneal step. At 10g, an a-SiC insulating layer was deposited on top of the conductive mesas via PECVD. At 10h, photoresist was patterned with photolithography and at 10i, the a-SiC was etched to form windows for the electrode sites using a reactive-ion etching (RIE) process. At 10j, a DRIE etch process through all the device layers and the oxide was performed to define the elongated probes followed by hydrofluoric acid (HF) processing to remove the elongated probes from the wafer at 10k.

Figure 2:
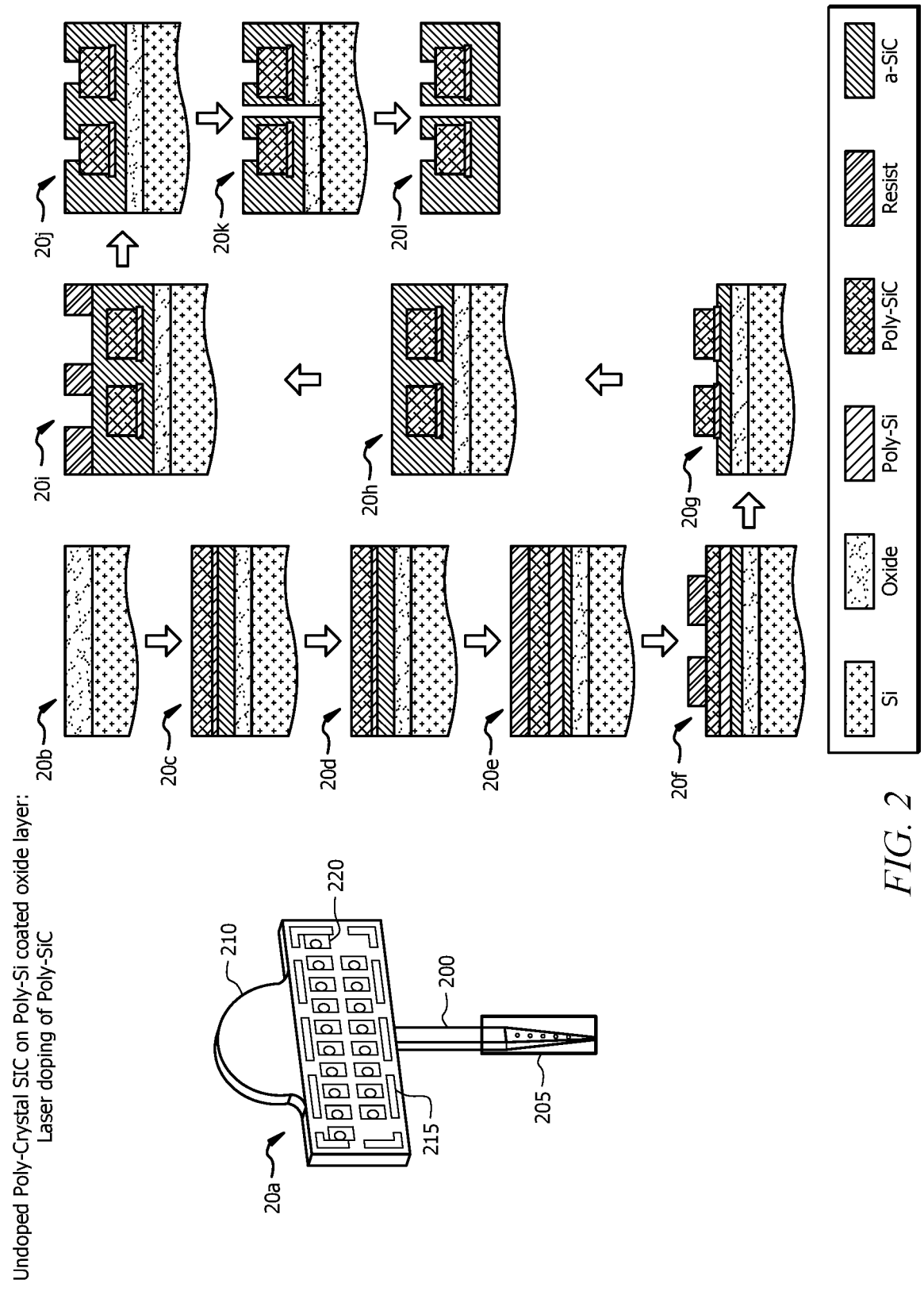
FIG. 2 illustrates an all-SiC fabrication process flow to fabricate implantable devices wherein the conductive poly-SiC layer is formed by laser doping, in accordance with an embodiment of the present invention.

FIG. 2 illustrates a second exemplary all-SiC fabrication process flow for the fabrication of a Michigan-style flexible monolithic all poly-SiC neural interface device 20a. The implantable neural interface device 20a provides for neural signal transduction with a brain of a subject of interest. The finished device 20a includes an elongated shaft 200 comprising a plurality of electrodes 205 formed by the illustrated process steps shown in 20b-20k and a probe base 210 integral with the elongated probe 200, the probe base 210 includes a plurality of contact pads 220, each of the plurality of contact pads 220 in electrical communication with one of the plurality of electrodes 205 via traces formed between the contact pads 220 and the electrodes 205. Various electronics for signal generation, switching control, signal filtering, digitization, wireless transmission, and power control may be coupled to the plurality of contact pads 220 of the probe base.

As illustrated in FIG. 2, the exemplary fabrication process flow begins at 20b by providing an oxide-coated Si Wafer. At 20c, a thick (~4 μm) a-SiC layer was deposited via PECVD, followed by the deposition of ~100 nm layer of poly-Si, followed by the growth of poly-SiC (undoped). At 20d, laser doping and annealing of the poly-SiC was performed to form conductive n-type poly-SiC. At 20e, the wafer was coated with photoresist and at 20f the photoresist was patterned via photolithography. At 20g, a DRIE process was used to form the conductive mesas of poly-SiC and at 20h, a thin a-SiC insulating layer was deposited on top of the conductive mesas via PECVD. At 20i, photoresist was then patterned with photolithography and at 20j, the a-SiC was etched to form windows for the electrode sites using an RIE process, at 20k, a DRIE etch process through all the device layers and the oxide was performed, followed by HF processing to remove the elongated probes from the wafer at 20l.

Figure 3:
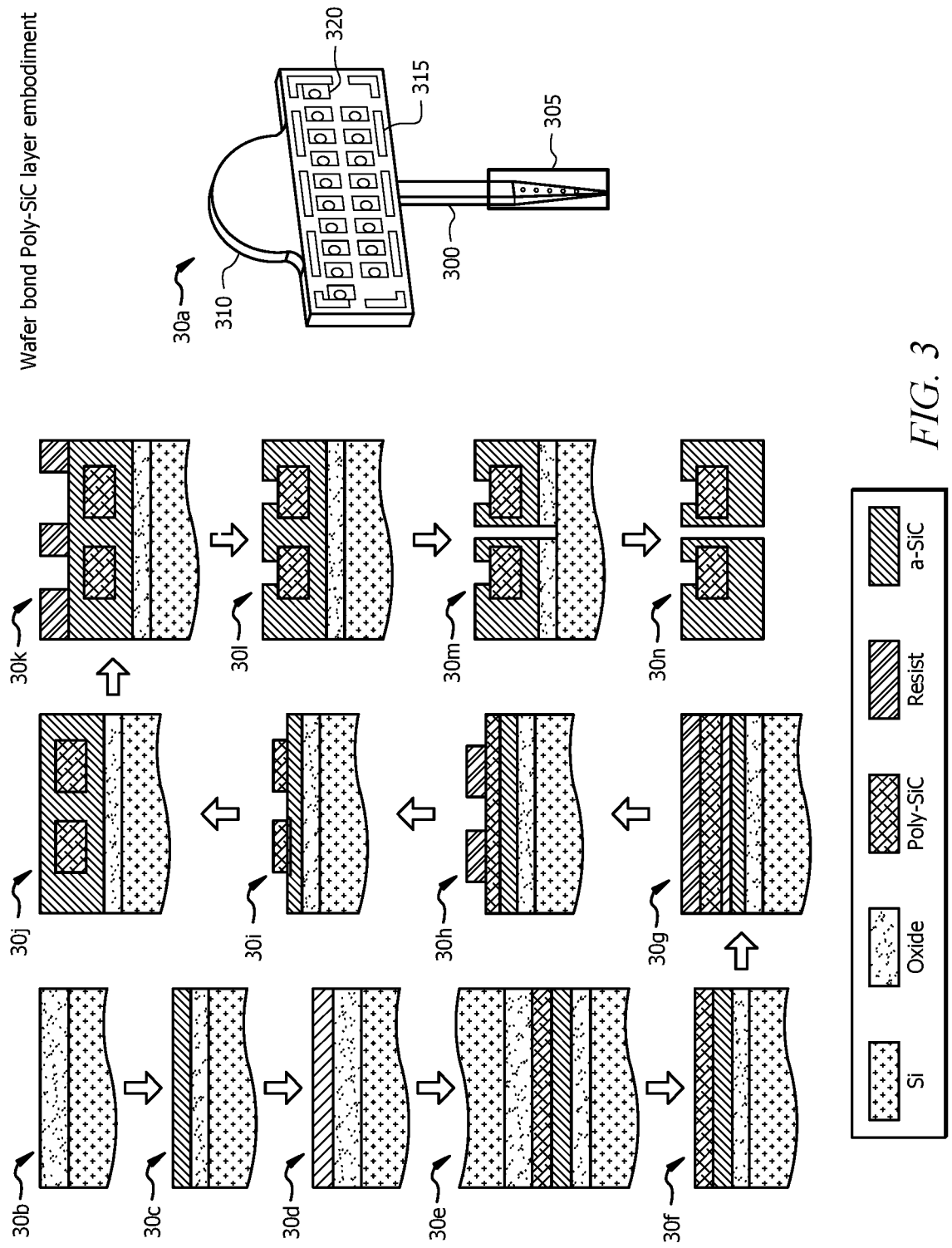
FIG. 3 illustrates an all-SiC fabrication process flow to fabricate implantable devices utilizing the bonding of two oxide-coated silicon wafers, in accordance with an embodiment of the present invention.

FIG. 3 illustrates a third exemplary all-SiC fabrication process flow for the fabrication of a Michigan-style flexible monolithic all poly-SiC neural interface device 30a. The implantable neural interface device 30a provides for neural signal transduction with a brain of a subject of interest. The finished device 30a includes an elongated shaft 300 comprising a plurality of electrodes 305 formed by the illustrated process steps shown in 30b-30k and a probe base 310 integral with the elongated probe 300, the probe base 310 includes a plurality of contact pads 320, each of the plurality of contact pads 320 in electrical communication with one of the plurality of electrodes 305 via traces formed between the contact pads 320 and the electrodes 305. Various electronics for signal generation, switching control, signal filtering, digitization, wireless transmission, and power control may be coupled to the plurality of contact pads 320 of the probe base.

As illustrated in FIG. 3, the exemplary fabrication process flow begins at 30b by providing two (2) oxide-coated Si wafers. At 30c, a thick (~4 μm) a-SiC layer was deposited via PECVD on one of the wafers. At 30d, a poly-SiC layer was grown (undoped or doped) on the other wafer. At 30e, the poly-SiC wafer was flipped and then bonded to the a-SiC wafer using a thermo-compression bond. At 30f, an HF etch was performed to remove the top handle wafer. At 30g a photoresist layer was spun and at 30h the photoresist layer was patterned for the conductive mesas. At 30i, a DRIE process was performed to form the conductive poly-SiC mesas and at 30j, the conductive poly-SiC mesas were coated with a thin a-SiC insulating layer via PECVD. At 30k a photoresist was spun and patterned with photolithography and at 30l, the a-SiC cap was etched to form windows for the tip and electrode sites using a RIE process. At 30m a photoresist was patterned and DRIE etched through all the device layers to form and define the elongated probe and at 30n, HF was used to release the elongated probes from handle wafer.

Figure 4:
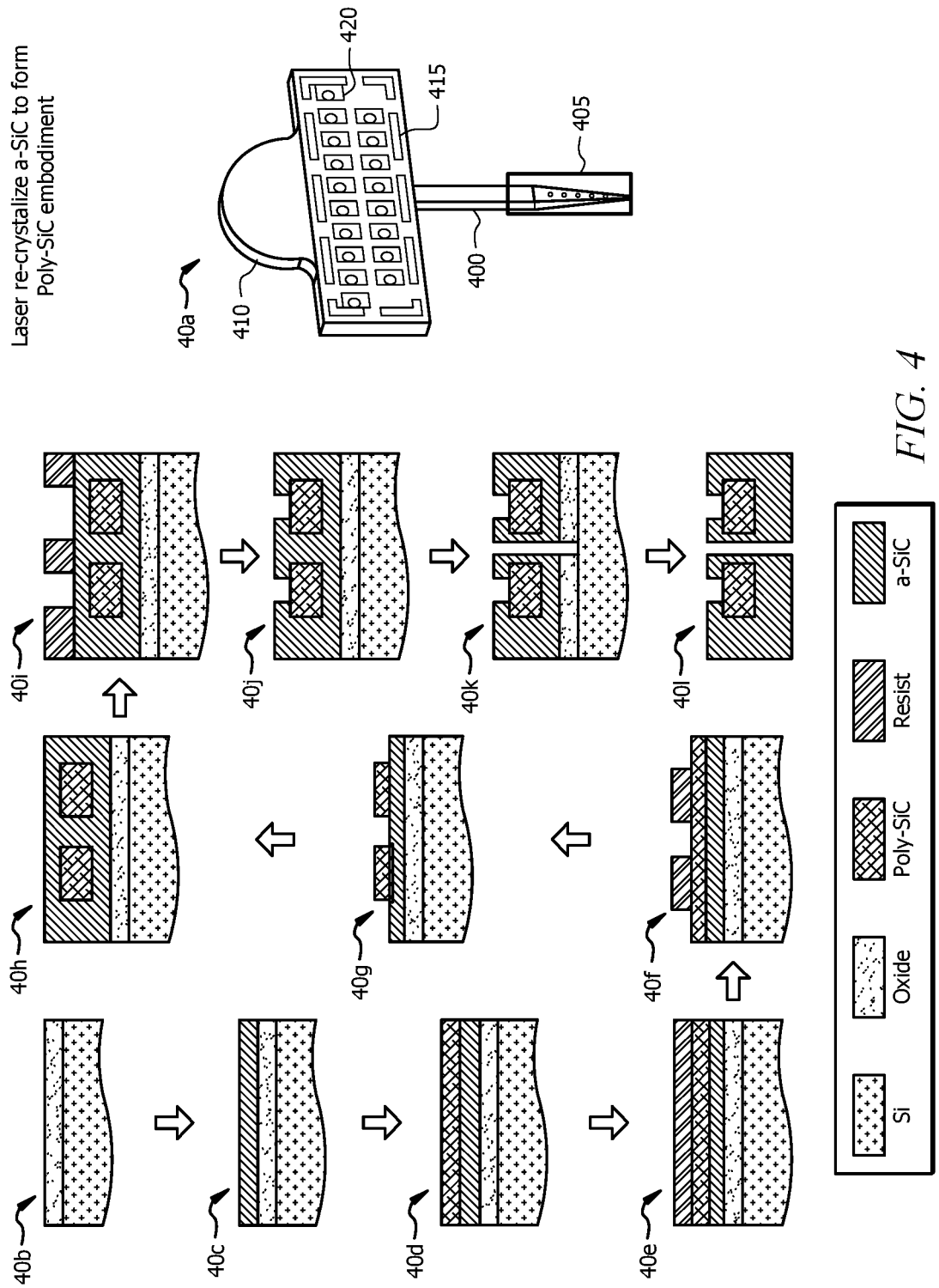
FIG. 4 illustrates an all-SiC fabrication process flow to fabricate implantable devices wherein the conductive poly-Sic is formed by laser recrystallization of the amorphous SiC layer, in accordance with an embodiment of the present invention.

FIG. 4 illustrates a third exemplary all-SiC fabrication process flow for the fabrication of a Michigan-style flexible monolithic all poly-SiC neural interface device 40a. The implantable neural interface device 40a provides for neural signal transduction with a brain of a subject of interest. The finished device 40a includes an elongated shaft 400 comprising a plurality of electrodes 305 formed by the illustrated process steps shown in 40b-40k and a probe base 410 integral with the elongated probe 400, the probe base 410 includes a plurality of contact pads 420, each of the plurality of contact pads 420 in electrical communication with one of the plurality of electrodes 405 via traces formed between the contact pads 420 and the electrodes 405. Various electronics for signal generation, switching control, signal filtering, digitization, wireless transmission, and power control may be coupled to the plurality of contact pads 420 of the probe base.

As illustrated in FIG. 3, the exemplary fabrication process flow begins at 40b by providing an oxide-coated Si wafer. At 40c, a thick (~6 μm) a-SiC layer was deposited via PECVD. At 40d, 2 μm of the a-SiC film was laser doped/re-crystalized to form doped poly-SiC on surface of the wafer. At 40e, photoresist was spun and at 40f, the photoresist was patterned to form mesa electrodes. At 40g, a DRIE process was used to form the conductive poly-SiC mesas and at 40h, the conductive poly-SiC mesas were coated with a thin a-SiC insulating layer, via PECVD, at 40i, photoresist was spun and patterned with photolithography and at 40j, the a-SiC cap was etched to form windows for the tip and electrode sites using a RIE process. At 40k, photoresist was patterned and DRIE etched through all device layers to form and define the elongated probe and at 40l, HF was used to release the elongated probes from handle wafer.

As show in FIG. 1-FIG. 4, the various exemplary processes produce the released, freestanding all poly-SiC electrode and elongated probes, which are then cleaned, as is commonly known in the art. The completed elongated probes are attached to the electronics via the contact pads on the probe base to facilitate signal transmission and recording. A fully implantable device includes electronics for conditioning and amplifying received signals (via amplifiers/filters, etc.), signal generation to excite an action potential from neurons or muscles (transmission), a control system to manage the signals, wireless communication, and power management. Power for the device can be either delivered with rechargeable batteries and/or inductive wireless generation. Although electronics can be generated in all poly-SiC, they can more easily be realized in Si. The latter method implies that Si electronics are realized separately and then attached (both electrically and physically) to the all poly-SiC device structure through standard semiconductor die bonding techniques. The vulnerable Si electronics are then hermetically sealed with a chemically resistive, low temperature deposition, biocompatible material, like amorphous silicon carbide, to protect it from attacks from the body's immune system. One way to archive this goal is to preserve part of the Si substrate upon which the all poly-SiC SiC grown upon for electronics implementation. The required electronics are realized in the preserved silicon probe base portion of the Michigan style probe and connected to the electrodes of the elongated probe through interconnections made using standard microelectronic processing (metal traces, insulation, conductive via connections, etc.). The device, consisting of signal and power electronics and at least one implantable elongated probe with at least one electrode, can be used as the main interface component of a brain machine interface (BMI) device.

As shown, the present invention provides a highly flexible, and therefore conformal, neural interface made exclusively out of neuro compatible SiC which allows for long-term, reliable bi-directional neural signal transduction to the human brain. By utilizing recent advances in low-temperature deposition and dopant control of polycrystalline SiC films, an all-SiC material stack can now be produced which, when processed using proven micromachining methods, will result in either planar conformal interfaces (e.g. ECoG) or implantable interfaces (e.g. INI). This will allow for long-term implantation in humans to treat such issues as Parkinson's, dementia, and neural damage, and additionally enable transparent bionics.

It is also to be understood that the following claims are intended to cover all of the generic and specific features of the invention herein described, and all statements of the scope of the invention which, as a matter of language, might be said to fall therebetween.

What is claimed is:

1. An implantable neural interface device for placement to provide neural signal transduction with a brain of a subject of interest, the device comprising:
   at least one elongated probe to be placed in a brain of a subject of interest, the at least one elongated probe comprising a plurality of electrodes positioned on a surface of the elongated probe, each of the plurality of electrodes comprising:
      a conductive mesa consisting of polycrystalline silicon carbide (poly-SiC);
      an insulative layer consisting of amorphous SiC, the insulative layer positioned to surround the conductive mesa absent a window through the amorphous SiC exposing a surface of the conductive mesa;
   a probe base integral with the elongated probe, the probe base comprising a plurality of contact pads, each of the plurality of contact pads in electrical communication with one of the plurality of electrodes; and
   one or more electrical traces connecting the plurality of electrodes to the plurality of contact pads of the probe base, wherein the one or more electrical traces consist of polycrystalline SiC.

2. The device of claim 1, wherein the elongated probe and the probe base are substantially flexible.

3. The device of claim 1, wherein the elongated probe is a Michigan-style probe.

* * * * *